United States Patent [19]

Ruehle

[11] Plant 4,118

[45] Oct. 4, 1977

[54] PISTACHIO TREE

[76] Inventor: Elmer C. Ruehle, 8599 Road 264, Terra Bella, Calif. 93270

[21] Appl. No.: 726,261

[22] Filed: Sept. 24, 1976

[51] Int. Cl.[2] ..... A01H 5/03

[52] U.S. Cl. ..... Plt./30

[58] Field of Search ..... Plt./30

*Primary Examiner*—Robert E. Bagwill

*Attorney, Agent, or Firm*—Huebner & Worrel

[57] ABSTRACT

A pistachio tree of the *Pistachia vera* species generally similar in appearance to the unpatented Kerman pistachio tree, but from which it is distinguished in bearing fruit of uniformly large size characterized by having thin shells with a higher percentage of naturally occurring split shells and with the split extending about the apex end of the shell rather than just along the side and which contains a kernel or nut meat having a bright green coloration extending uniformly throughout the meat and which ripens earlier than the Kerman, Red Allepo and Trabonella pistachios and at about the same time as the Bronte pistachio all of which to the applicant's knowledge are unpatented.

2 Drawing Figures

ORIGIN

The pistachio tree of the present invention occurred as a chance seedling believed to be of parentage consisting of probably a Bronte pistachio and an unknown male in an orchard of other pistachio seedlings at 8599 Road 264, near the city of Terra Bella, County of Tulare and the state of California, owned by Elmer C. Ruehle and Adolph J. Ruehle the last of whom is now deceased.

DISCOVERY

The new variety was discovered in the orchard by the applicant, Elmer C. Ruehle, where its distinctive characteristics attracted his attention.

ASEXUAL REPRODUCTION

After observing the new variety, the applicant, Elmer C. Ruehle, budded selected buds from the new variety into host trees in his orchard identified above. The buds grew successfully and were carefully observed. They were found to maintain the characteristics of the originally discovered seedling in all observable respects.

SUMMARY

*Pistachia vera* is the species of the Pistachia genus which has been found suitable for commercial nut production. This species alone has been found suitable for commercial use, in part, because the nuts produced have higher degrees of splitting along the suture of the bony endocarp or shell of the nut than other species of the Pistachia genus. *Pistachia vera* are native to the arid portions of Asia and Asia Minor and are grown in the Mediterranean area, Turkey, Iran and Afghanistan as a nut crop. No significant commercial industry has yet developed in the United States although *Pistachia vera* can be raised in California and the arid Southwestern portions of the United States. Extensive plantings have been made in the San Joaquin Valley of California, particularly in the Counties of Madera, Kings and Kern but such orchards are only starting to produce.

The pistachio tree of the present invention generally possesses the appearance of the Kerman pistachio tree with respect to vigor of growth, size and heavy bearing and in the production of fruit of generally similar outward appearance but being generally more oblong and rounded, having generally greenish yellow outer husks having a pink to purple coloration over substantial portions thereof when ripe.

The pistachio tree of the present invention is distinct from the Kerman pistachio tree in that it bears fruit in which the meat of the nut is substantially uniformly bright green in appearance extending throughout the meat and in which the bony endocarp or shell of the nuts split naturally in a substantially greater percentage of cases than any known pistachio variety. Furthermore, in the pistachio tree of the present invention the splitting commonly occurs about the apex end of the shell rather than only along the side of the shell as in the Kerman variety. The pistachio tree of the present invention produces nuts which ripen earlier than the nuts of the Kerman pistachio variety by nearly one full month and about the same time as the Bronte pistachio variety.

The new variety begins to bloom in early April at about the same time as the Red Allepo, Bronte and Trabonella *Pistachia vera* usually on the first of April. This is approximately six days earlier than the Kerman *Pistachia vera.* The new variety is dioecious, as are all *Pistachia vera,* normally requiring pollen bearing Pistachia varieties of trees to be planted along with the nut bearing trees, or that artificial pollenation to be provided. The blossoms are of a size typical for conventional varieties of *Pistachia vera,* being very small and appearing in clusters of a dark cream color.

BRIEF DESCRIPTION OF THE DRAWINGS

The accompanying drawings are color photographs of the new variety:

First Drawing:

Figure 1:
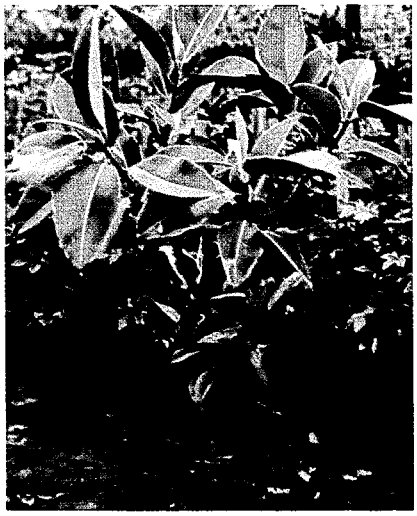
Figure 2A:
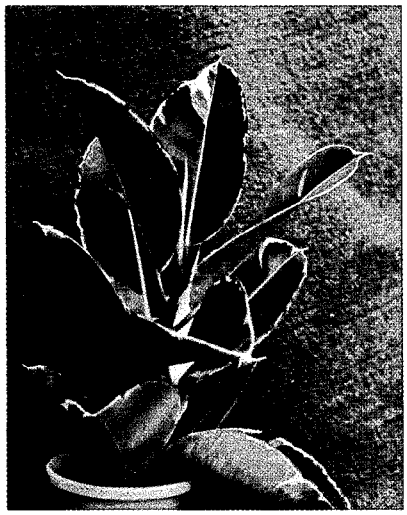
Figure 2B:
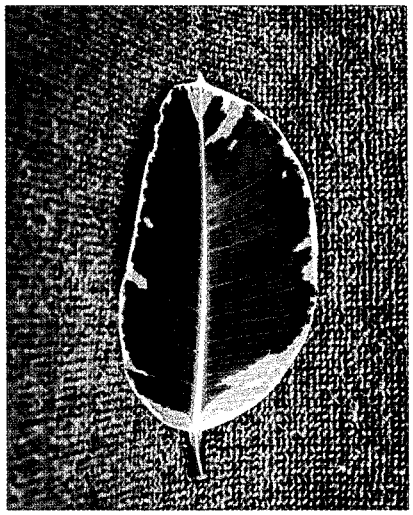
Figure 3A:
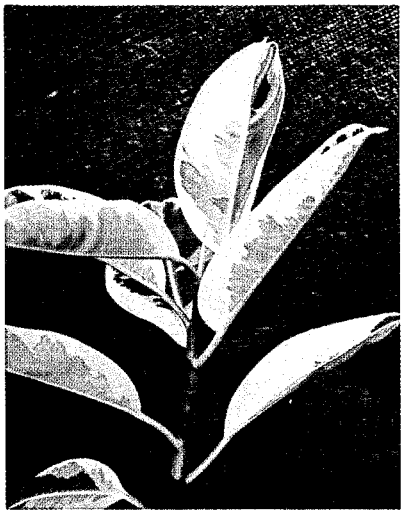
Figure 3B:
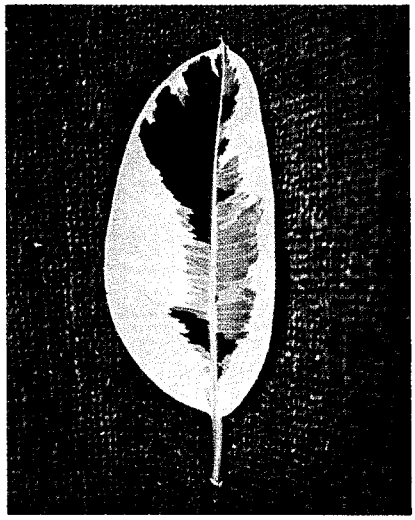

1. two branches, one bearing foilage typical of the present variety and the other bearing fruit in a cluster typical of that having reached maturity;

Second Drawing:

1. a single whole fruit of the present variety characteristic of those having reached a ripened condition;

2. a single fruit having had the husk removed to expose the nut and having typical naturally occurring splitting of the shell about the apex end of the shell and showing a characteristically high ratio of kernel size to shell size;

3. an end view of a nut of the new variety;

4. the kernel or nut meat of the new variety showing the characteristic pink to purple coloration of the pellicle or seed coat;

5. a kernel with the seed coat removed to show the brilliant green exterior appearance;

6. two kernel halves having been severed along the suture plane to show the uniformly green nut meat coloration; and 7. two kernel halves having been severed along a plane transverse to the suture plane.

DESCRIPTON OF THE NEW VARIETY

Referring in greater detail to the pomological characteristics of the present variety of pistachio tree, its characteristics are set forth as observed under the ecological provisions prevailing at the applicant's orchard designated above. The major color plate numerical identificatons are by reference to the Nickerson Color Fan of the American Horticultural Council.

TREE

Size: Generally small and typical of all *Pistachia vera* at maturity being roughly 25 feet in height and 25 feet in diameter with vigorous growth.

Figure: Rounded and squatty in appearance, but with the precise shape and size determined by pruning practices.

Productivity: Good being roughly equivalent to the Kerman *Pistachia vera.*

Regularity of bearing: Normal and about the same as the Kerman *Pistachia vera.*

Trunk:

*Diameter.*—Approximately 30 cm.

*Surface characteristics.*—Rough with gray brown coloration after fifth or sixth year of growth.

Branches:

*Size.*—About the same as the Kerman *Pistachia vera.*

*Surface character.*—Rough.

*Color.*—Brown with overlying grayish hue on older branches, underlying greenish hue in younger branches.

*Lenticels.*—Numerous and of medium size.

Leaves:

*Size.*—Standard for *Pistachia vera.*

*Length.*—Varying from 5 cm. to 11.5 cm. with the average being about 8 cm.

*Width.*—Varying from 3 cm. to 7.5 cm. while averaging about 5 cm.

*Shape.*—Rounded mucronate to cuspidate with slight tip being roughly elliptic in shape.

*Type.*—Trifoliate.

*Color.*—Moderate yellow green (7.5 GY 5/7) to moderate olive green (7.5 GY 4/4).

*Marginal form.*—Entire.

*Petiole.*—Length: 6 cm. Thickness: 2 cm. to 3 cm.

*Stipules.*—None.

FLOWER BUDS

Size: Normal to larger than Kerman *Pistachia vera.*

Shape: Substantially conical.

Surface: Normal for *Pistachia vera.*

FLOWERS

Dates of bloom: First 2 weeks in April at Terra Bella, Calif.

Size: Normal for *Pistachia vera* and thus very small, but growing in clusters.

Color: Dark Cream.

Fertile: Dioecious.

FRUIT

Maturity: September 15 in Terra Bella, Calif. and thus being about the same time as Bronte *Pistachia vera* and 5 days earlier than Red Allepo *Pistachia vera,* 16 days earlier than Trabonella *Pistachia vera* and 25 days earlier than Kerman *Pistachia vera.*

Size: Large.

*Uniformity.*—Great uniformity with size being medium to large and almost identical compared to Kerman *Pistachia vera.*

*Axial Diameter.*—2.5 cm.

*Diameter transverse in suture plane.*—1.5.

*Diameter transverse at right angles to suture plane.*—1.4 cm.

Husk:

*Thickness.*—1 mm. to 2 mm.

*Color.*—Brilliant yellow green (2.5 GY 9/8) with white spots and pink to purplish coloration extending over portions of surface varying from strong purplish pink (7.5 RP 7/10) to strong purplish red (7.5 RP 5/12).

Shell:

*Shape.*—Similar to Bronte and Trabonella *Pistachia vera.*

*Color.*—White to slightly yellowish brown.

*Thickness.*—0.5 mm. to 1 mm.

*Form.*—Approximately 90 percent of all shells are naturally split about the toward base end of shell in many cases, as in the drawing, reaching almost to the base on both sides of the shell.

Seed or kernel:

*Form.*—Single Kernel per nut enclosed in pellicle and having no flap. Higher ratio of kernel by size and weight to shell, than in those of Kerman *Pistachia vera.*

*Pellicle or seed coat.*—Thin and minutely veined being of a light brown to green coloration with large purplish red (10 RP 3/10) portions extending over most of the surface.

*Meat.*—Generally uniformly green throughout. External color with pellicle removed is generally brilliant green varying from strong yellow green (5 GY 6/8) to moderate yellow green (5 GY 5/6). Along the suture plane the color varies from brilliant yellow green (5 GY 8/8) to strong yellow green (5 GY 6/8). Very good eating quality having a slightly sweeter flavor than meat of the Kerman *Pistachia vera* slightly more dense and having more of a snap than Kerman *Pistachia vera* when bitten into.

RESISTANCE TO INSECTS AND DISEASE

About equally susceptible to insects as Kerman *Pistachia vera,* but much less susceptible to Epicarp Lesion.

USE

Sun, air, or artificially dried. Can be roasted, salted, diced and the like. It is believed that the new variety of the present invention will be highly advantageous for commercial utilization in view of the high percentage of natural shell splitting which requires little further processing. Furthermore, since such splitting occurs about the apex ends of the shells and along their sides, the shells are much easier to remove. Additionally, the uniformly green coloration of the nut meat and its good flavor enhances its sales appeal.

KEEPING QUALITY

**Very good and typical for other *Pistachia vera* in that the nut meat can be preserved by drying for long periods of time.**

It is to be understood that the pistachio tree and its fruit described above may vary in response to variations in climate, soil and cultural conditions. However, when grown with proper farming techniques under the ecological conditions prevailing in the general vicinity of Terra Bella, Calif., its characteristics are as described above.

What is claimed is:

1. A new and distinct variety of pistachio tree of the *Pistachia vera* species substantially as illustrated and described which is generally similar in appearance to the Kerman pistachio tree and which produces fruit of uniformly large size characterized by having relatively thin shells with a higher percentage of natural shell splitting than the Kerman pistachio with the splitting occurring about the apex ends of the shells, which contain nut meat having a high meat to shell ratio by size and weight and characterized by a brilliant green exterior coloration extending in lighter shades throughout the meat and which ripen earlier than the Kerman, Red Allepo and Trabonella pistachios and at about the same time as the Bronte pistachio.

* * * * *

UNITED STATES PATENT AND TRADEMARK OFFICE

CERTIFICATE OF CORRECTION

PATENT NO. : PP4118

DATED : October 4, 1977

INVENTOR(S) : Elmer C. Ruehle

It is certified that error appears in the above-identified patent and that said Letters Patent are hereby corrected as shown below:

Replace the incorrect drawings with the drawing as shown per attachment.

Column 4, Line 33, after "the" and before "toward" insert

--- apex end of shell and along sides ---.

Signed and Sealed this

*Thirty-first* Day of *January 1978*

[SEAL]

*Attest:*

RUTH C. MASON
*Attesting Officer*

LUTRELLE F. PARKER
*Acting Commissioner of Patents and Trademarks*